United States Patent

Heil et al.

[11] Patent Number: 6,008,366
[45] Date of Patent: Dec. 28, 1999

[54] ACYLATED 5-AMINOISOTHIAZOLES WITH INSECTICIDAL PROPERTIES, INTERMEDIATE PRODUCTS AND PROCESS FOR PRODUCING THEM

[75] Inventors: Markus Heil, Leverkusen; Christoph Erdelen, Leichlingen; Ulrike Wachendorff-Neumann, Neuwied; Andreas Turberg, Haan; Norbert Mencke, Leverkusen, all of Germany

[73] Assignee: Bayer Aktiengesellschaft, Leverkusen, Germany

[21] Appl. No.: 09/338,484

[22] Filed: Jun. 22, 1999

Related U.S. Application Data

[62] Division of application No. 09/068,598, filed as application No. PCT/EP96/04796, Nov. 4, 1996.

[30] Foreign Application Priority Data

Nov. 14, 1995 [DE] Germany .......................... 195 42 372

[51] Int. Cl.$^6$ ................................................. C07D 275/03
[52] U.S. Cl. ............................................ 548/214; 548/213
[58] Field of Search ...................... 548/213, 214

[56] References Cited

U.S. PATENT DOCUMENTS 5,538,939  7/1996  Muenster et al. ...................... 504/269

FOREIGN PATENT DOCUMENTS

| 0 334 809 | 9/1989 | European Pat. Off. . |
| 0 623 282 | 3/1995 | European Pat. Off. . |
| 640597 | 3/1995 | European Pat. Off. . |
| 2 014 527 | 4/1970 | France . |
| 95/31448 | 11/1995 | WIPO . |

OTHER PUBLICATIONS

Chem. Ber. Vo. 96, Feb. 1963. Weinheim, pp. 526–533, Goerdeler J. et al., "Darstellung und Cyclisierung von Alpha–Acyl–beta–amino–thiocrotonamiden".

Chem. Ber. vol. 97, Oct. 1964, Weinheim, pp. 3106–3117, Goerdeler J. et al., "Synthese von 5–amino–3–hydroxy(alkoxy–,amino–) isothiazo len und von Derivaten der Pyrimidinthione–(4)".

Indian J. Chem., vol. 16B, Sep. 1978, pp. 752–754, Rajappa, S. et al., "Synthesis of Thiophenes: Part VI—Synthesis of 2–Nitro–& 2,4–Dinitrothiophenes by direct Ring–closure Reactions".

J. Org. Chem., vol. 42, No. 20, 1997, Washington, pp. 3230–3233, Howe, R.K.: "Reaction of Ethyl–beta–Aminocrotonate with Trichloromethanesulfenyl Chloride".

*Primary Examiner*—Laura L. Stockton
*Attorney, Agent, or Firm*—Sprung Kramer Schaefer & Briscoe

[57] ABSTRACT

The present invention relates to novel acylated 5-aminoisothiazoles of the formula

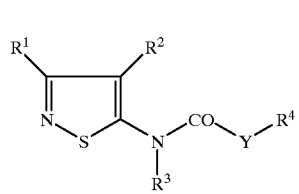

(I)

in which $R^1$, $R^2$, $R^3$, $R^4$ and Y have the meaning given in the description, processes for their preparation and their use for controlling animal pests.

1 Claim, No Drawings

ACYLATED 5-AMINOISOTHIAZOLES WITH INSECTICIDAL PROPERTIES, INTERMEDIATE PRODUCTS AND PROCESS FOR PRODUCING THEM

This is a division of application Ser. No. 09/068,598, filed on May 11, 1998, now allowed, which is a 371 of PCT/EP96/04796, filed on Nov. 4, 1996.

The present invention relates to novel acylated 5-aminoisothiazoles, processes for their preparation and their use for controlling animal pests.

It is already known that certain acylated 4-cyano-5-aminoisothiazoles have insecticidal properties (cf., for example, EP-A 0 623 282).

However, the activity and range of action of these compounds are not always completely satisfactory, especially when low amounts are applied and at low concentrations.

Novel acylated 5-aminoisothiazoles of the formula (I)

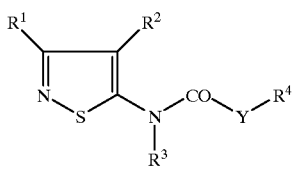

(I)

in which
R$^1$ represents alkyl, halogenoalkyl, alkoxyalkyl, alkylthioalkyl, alkoxy, alkylthio or optionally substituted cycloalkyl,
R$^2$ represents hydrogen, halogen, cyano, nitro, thiocyanato, alkoxycarbonyl, alkenyloxycarbonyl, alkylthio, halogenoalkylthio, alkylsulfinyl, halogenoalkyl sulfinyl, alkylsulfonyl, halogenoalkylsulfonyl or thiocarbamoyl,
R$^3$ represents hydrogen, alkyl, halogenoalkyl, alkoxyalkyl, alkylcarbonyl, alkylsulfonyl, in each case optionally substituted arylcarbonyl, arylsulfonyl or arylalkyl or optionally substituted cycloalkyl,
R$^4$ represents optionally substituted aryl, optionally substituted cycloalkyl or optionally substituted cycloalkenyl and
Y represents optionally substituted alkylene, alkenylene or alkylenoxy, have now been found.

It has furthermore been found that the acylated 5-aminoisothiazoles of the formula (I) are obtained by a process in which
a) 5-aminoisothiazoles of the formula (II)

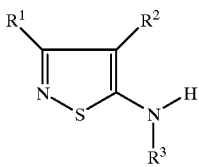

(II)

in which
R$^1$, R$^2$ and R$^3$ have the above-mentioned meaning, are reacted with acid halides of the formula (III)

R$^4$—Y—CO—Hal    (III)

in which

R$^4$ and Y have the above-mentioned meaning and
Hal represents halogen, in the presence of a base and in the presence of a diluent; or
b) acylated 5-aminoisothiazoles of the formula (Ia)

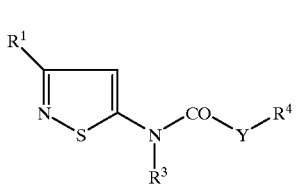

(Ia)

in which
R$^1$, R$^3$, R$^4$ and Y have the above-mentioned meaning,
(α) are reacted with a halogenating agent, if appropriate in the presence of a diluent and if appropriate in the presence of a catalyst, or
(β) are reacted with a nitrating reagent, if appropriate in the presence of a diluent, or
c) β-amino-thiocrotonamides of the formula (IV)

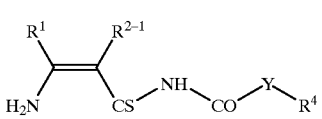

(IV)

in which
R$^1$, R$^4$ and Y have the above-mentioned meaning and
R$^{2-1}$ represents cyano or alkoxycarbonyl, are cyclized with an oxidizing agent, if appropriate in the presence of a diluent.

Finally, it has been found that the novel acylated 5-aminoisothiazoles of the formula (I) have highly pronounced biological properties, and above all are suitable for controlling animal pests, in particular insects, arachnids and nematodes, which occur in agriculture, in forestry, in the preservation of stored products and materials and in the hygiene sector.

The formula (I) provides a general definition of the acylated 5-aminoisothiazoles according to the invention.

Preferred substituents and ranges of the radicals listed in the formulae mentioned above and below are explained in the following.

R$^1$ preferably represents C$_1$–C$_4$-alkyl, C$_1$–C$_4$-halogenoalkyl having 1 to 5 identical or different halogen atoms, such as fluorine, chlorine and bromine atoms, C$_1$–C$_4$-alkoxy-C$_1$–C$_4$-alkyl, C$_1$–C$_4$-alkylthio-C$_1$–C$_4$-alkyl, C$_1$–C$_4$-alkoxy or C$_1$–C$_4$-alkylthio, or represents C$_3$–C$_6$-cycloalkyl which is optionally substituted once to three times in an identical or different manner by C$_1$–C$_4$-alkyl or halogen.

R$^2$ preferably represents hydrogen, halogen, cyano, nitro, thiocyanato, C$_1$–C$_4$alkoxy-carbonyl, C$_2$–C$_4$-alkenyloxy-carbonyl, C$_1$–C$_4$-alkylthio, C$_1$–C$_4$-halogenoalkylthio having 1 to 5 identical or different halogen atoms, such as fluorine and chlorine atoms, C$_1$–C$_4$-alkylsulfinyl, C$_1$–C$_4$-halogenoalkylsulfinyl having 1 to 5 identical or different halogen atoms, such as fluorine and chlorine atoms, C$_1$–C$_4$-alkylsulfonyl or C$_1$–C$_4$-halogenoalkylsulfonyl having 1 to 5 identical or different halogen atoms, such as fluorine and chlorine atoms, or represents thiocarbamoyl.

R$^3$ preferably represents hydrogen, C$_1$–C$_4$-alkyl, C$_1$–C$_4$-halogenoalkyl having 1 to 5 identical or different halogen atoms, such as fluorine and chlorine atoms, $C_1$–$C_4$-alkoxy-$C_1$–$C_4$-alkyl, $C_1$–$C_4$-alkyl-carbonyl, $C_1$–$C_4$-alkylsulfonyl or phenylcarbonyl, phenylsulfonyl or benzyl, in each case optionally substituted in the phenyl ring once to three times in an identical or different manner, possible substituents in each case being halogen, nitro, cyano, $C_1$–$C_4$-alkyl, $C_1$–$C_2$-halogenoalkyl having 1 to 5 identical or different halogen atoms, such as fluorine and chlorine atoms, $C_1$–$C_4$-alkoxy, $C_1$–$C_4$-alkylthio, $C_1$–$C_2$-halogenoalkoxy having 1 to 5 identical or different halogen atoms, such as fluorine and chlorine atoms, or $C_1$–$C_2$-halogenoalkylthio having 1 to 5 identical or different halogen atoms, such as fluorine and chlorine atoms, or represents $C_3$–$C_6$-cycloalkyl which is optionally substituted once to three times in an identical or different manner by $C_1$–$C_4$-alkyl or halogen.

$R^4$ preferably represents phenyl which is optionally substituted once to three times in an identical or different manner, possible substituents being halogen, nitro, cyano, $C_1$–$C_{12}$-alkyl, $C_1$–$C_{12}$-halogenoalkyl having 1 to 5 identical or different halogen atoms, such as fluorine and chlorine atoms, $C_1$–$C_{12}$-alkoxy, $C_1$–$C_{12}$-halogenoalkoxy having 1 to 5 identical or different halogen atoms, such as fluorine and chlorine atoms, $C_1$–$C_{12}$-alkylthio, $C_1$–$C_{12}$-halogenoalkylthio having 1 to 5 identical or different halogen atoms, such as fluorine and chlorine atoms, $C_2$–$C_{12}$-alkenyl, $C_2$–$C_{12}$-halogenoalkenyl having 1 to 5 identical or different halogen atoms, such as fluorine and chlorine atoms, $C_3$–$C_8$-cycloalkyl which is optionally substituted once to three times in an identical or different manner by $C_1$–$C_4$-alkyl or halogen, and phenyl, phenoxy, phenylthio, benzyl or benzyloxy, in each case optionally substituted once to three times in an identical or different manner by halogen, nitro, cyano, $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_1$–$C_4$-alkylthio-$C_1$–$C_4$-alkyl, $C_1$–$C_4$-alkylsulfonyl, $C_1$–$C_4$-halogenoalkylsulfonyl having 1 to 5 identical or different halogen atoms, such as fluorine and chlorine atoms, $C_1$–$C_4$-alkylcarbonyl, $C_1$–$C_4$-alkoxy-carbonyl, thioamide, $C_1$–$C_4$-alkoximino-$C_1$–$C_4$-alkyl or optionally $C_1$–$C_4$-alkyl-substituted oxdiazolyl, or represents $C_3$–$C_8$-cycloalkyl or $C_5$–$C_8$-cycloalkenyl, in each case optionally substituted once to three times in an identical or different manner, possible substituents being $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_3$–$C_8$-cycloalkyl and phenyl which is optionally substituted once to three times in an identical or different manner by halogen, cyano, nitro, $C_1$–$C_4$-alkyl, $C_1$–$C_4$-halogenoalkyl having 1 to 5 identical or different halogen atoms, such as fluorine and chlorine atoms, $C_1$–$C_4$-alkoxy or $C_1$–$C_4$-halogenoalkoxy having 1 to 5 identical or different halogen atoms, such as fluorine and chlorine atoms.

Y preferably represents $C_1$–$C_6$-alkylene, $C_1$–$C_6$-hydroxyalkylene, $C_1$–$C_4$-alkoxy-$C_1$–$C_6$-alkylene, $C_1$–$C_4$-alkylcarbonyloxy-$C_1$–$C_6$-alkylene, cyano-$C_1$–$C_6$-alkylene or $C_1$–$C_4$-halogenoalkylene having 1 to 5 identical or different halogen atoms, such as fluorine and chlorine atoms; or $C_3$–$C_6$-cycloalkyl-$C_1$–$C_4$-alkylene, $C_2$–$C_4$-alkenylene or $C_1$–$C_4$-alkenyloxy which are optionally substituted once to three times in an identical or different manner by fluorine, chlorine or methyl.

$R^1$ particularly preferably represents methyl, ethyl, n- or i-propyl or n-, i-, s- or, t-butyl $CH_2F$, $CHF_2$, $CF_3$, $CH_2Cl$, $CH_2Br$ or $CHClCH_3$; methoxy, ethoxy, methoxymethyl or ethoxymethyl; methylthiomethyl or cyclopropyl.

$R^2$ particularly preferably represents hydrogen, chlorine, bromine, cyano, nitro or thiocyanato; methoxycarbonyl, ethoxycarbonyl, i-propoxycarbonyl or n-propoxycarbonyl; allyloxycarbonyl; $SCF_3$, $SCCl_2F$, $SOCF_3$, $SOCCl_2F$, $SO_2CF_3$, $SO_2CCl_2F$, $SCHF_2$, $SOCHF_2$, $SO_2CHF_2$ or $CSNH_2$.

$R^3$ particularly preferably represents hydrogen, methyl, ethyl or n- or i-propyl; methoxymethyl, ethoxymethyl, n-propoxymethyl or n-butoxymethyl; methylcarbonyl or methylsulfonyl; phenylcarbonyl or benzyl, in each case optionally substituted once or twice in an identical or different manner by fluorine, chlorine, methyl or trifluoromethyl; or cyclopropyl.

$R^4$ particularly preferably represents phenyl which is optionally substituted once to three times in an identical or different manner, possible substituents being halogen, nitro, cyano, $C_1$–$C_{12}$-alkyl, $C_1$–$C_{12}$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine and chlorine atoms, $C_2$–$C_4$-alkenyl, $C_2$–$C_4$-halogenoalkenyl having 1 to 5 identical or different halogen atoms, such as fluorine and chlorine atoms, and phenoxy, phenylthio or benzyloxy, in each case optionally substituted once to three times in an identical or different manner by halogen, nitro, cyano, $C_1$–$C_4$-alkyl, $C_1$–$C_4$-halogenoalkyl having 1 to 5 identical or different halogen atoms, such as fluorine and chlorine atoms, $C_1$–$C_4$-alkoxy, $C_1$–$C_4$-halogenoalkoxy having 1 to 5 identical or different halogen atoms, such as fluorine and chlorine atoms, $C_1$–$C_4$-alkylthio, $C_1$–$C_4$-halogenoalkylthio having 1 to 5 identical or different halogen atoms, such as fluorine or chlorine atoms, $C_1$–$C_4$-alkylthio-$C_1$–$C_4$-alkyl, $C_1$–$C_4$-alkylsulfonyl, $C_1$–$C_4$-halogenoalkylsulfonyl having 1 to 5 identical or different halogen atoms, such as fluorine or chlorine atoms, $C_1$–$C_4$-alkyl-carbonyl, $C_1$–$C_4$-alkoxy-carbonyl, thioamide, $C_1$–$C_4$-alkoximino-$C_1$–$C_2$-alkyl or optionally $C_1$–$C_2$-alkyl-substituted 1,2,4-oxdiazol-3-yl.

Y particularly preferably represents one of the groups —$CH_2$—, —$CH(CH_3)$—, —$CH(C_2H_5)$—, —$CH(n$—$C_3H_7)$—, —$CH(i$—$C_3H_7)$—, —$CH_2CH_2$—, —$CH(OH)$—, —$CH(OCH_3)$—, —$CH(O$—$CO$—$CH_3)$—, —$CH(CN)$—, —$CHF$—, —$CHCl$—,

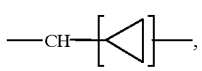,

—CH=CH— or —$CH_2O$—.

$R^1$ especially preferably represents methyl, ethyl, n- or i-propyl or n-, s- or t-butyl; $CH_2F$, $CF_3$, $CH_2Cl$, $CH_2Br$, methoxy or ethoxy.

$R^2$ especially preferably represents hydrogen, chlorine, bromine, cyano, nitro, thiocyanato, methoxycarbonyl, ethoxycarbonyl, $SCF_3$, $SOCF_3$ or $SO_2CF_3$.

$R^3$ especially preferably represents hydrogen, methyl, ethyl, methoxymethyl, ethoxymethyl, methylcarbonyl, phenylcarbonyl or methylsulfonyl.

$R^4$ especially preferably represents phenyl which is optionally substituted once to three times in an identical or different manner, possible substituents being fluorine, chlorine, bromine, nitro, cyano, methyl, ethyl, n- or i-propyl or n-, i-, s- or t-butyl; methoxy, ethoxy, n- or i-propoxy or n-, i-, s- or t-butoxy; methylthio, $CF_3$, $OCF_3$, $OCHF_2$, $SCF_3$ or $SCCl_2F$; $CH_2Br$ or $CH_2Cl$, and phenoxy or benzyloxy which are optionally substituted once to three times in an identical or different manner by fluorine, chlorine, bromine, nitro, cyano, methyl, ethyl, n- or i-propyl, n-, i-, s- or t-butyl, methoxy, ethoxy, n- or i-propoxy, n-, i-, s- or t-butoxy, methylthio, methylthiomethyl, $CF_3$, $OCF_3$, $OCHF_2$, $SCF_3$, $SCCl_2F$, $CH_2Br$, $CH_2Cl$, acetyl, ethylcarbonyl, methoxycarbonyl, methylsulfonyl, trifluoromethysulfonyl, thioamide, methoximomethyl, 1-(methoximino)ethyl, 1-(ethoximino)ethyl, 1,2,4-oxdiazol-3-yl or 5-methyl-1,2,4-oxdiazol-3-yl.

Y especially preferably represents —$CH_2$—, —$CH(CH_3)$— or —$CH_2O$—, in particular —$CH_2$— or —$CH(CH_3)$—.

Preferred compounds according to the invention are substances of the formulae (IA) or (IB):

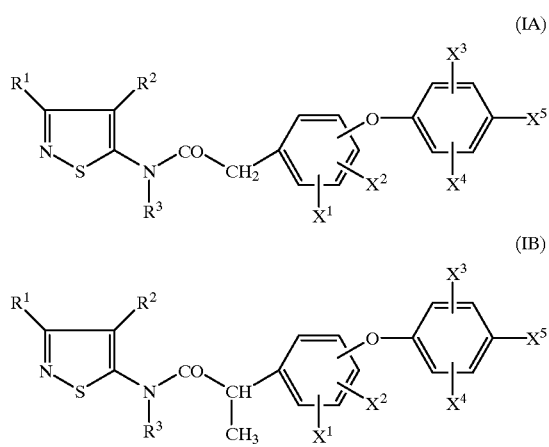

in which $R^1$, $R^2$ and $R^3$ represent the above-mentioned general, preferred, particularly preferred and especially preferred meanings and $X^1$, $X^2$, $X^3$, $X^4$ and $X^5$ represent the substituents mentioned above, under $R^4$, generally, preferably, particularly preferably and especially preferably for the phenyl or phenoxy radical and $X^1$, $X^2$, $X^3$ and $X^4$ in each case can also represent hydrogen.

Another preferred group of compounds are those of the formulae (IA) or (IB) in which the phenoxy radical is in the para-position relative to the $NR^3$—CO—$CH_2$— or $NR^3$—COCH($CH_3$)— group, among these compounds, those in which the substituents $X^1$, $X^2$, $X^3$ and $X^4$ represent hydrogen being particularly preferred.

Another preferred group of compounds are those in which $R^1$ represents alkoxyalkyl, alkylthioalkyl, alkylthio or optionally substituted cycloalkyl.

Another preferred group of compounds are those in which $R^3$ represents alkylsulfonyl or in each case optionally substituted arylcarbonyl, arylsulfonyl or cycloalkyl.

Another preferred group of compounds are those in which $R^4$ represents phenyl which is substituted by benzyloxy optionally substituted as described above, the benzyloxy radical preferably being in the para-position relative to the substituent already present on the phenyl ring.

Another group of preferred compounds are those in which $R^2$ represents cyano, nitro, thiocyanato, alkoxycarbonyl, alkenyloxycarbonyl, alkylthio, halogenoalkylthio, alkylsulfinyl, halogenoalkylsulfinyl, alkylsulfonyl, halogenoalkysulfonyl or thiocarbamoyl, in particular cyano.

Another group of preferred compounds are those of the formulae (IA) or (IB) in which $X^5$ represents alkylthio, halogenoalkylthio, alkylthioalkyl, alkylsulfonyl, halogenoalkylsulfonyl, alkoxycarbonyl, thioamide, alkoximinoalkyl or optionally alkyl-substituted oxdiazolyl, wherein the particular number of carbon atoms is mentioned above under $R^4$ and $X^1$, $X^2$, $X^3$ and $X^4$ in particular represent hydrogen.

The above-mentioned general definitions of radicals and explanations are those given in preferred ranges apply accordingly to the end product and to the starting substances and intermediates. These definitions of radicals can be combined with one another as desired, that is to say also between the particular preferred ranges.

Compounds of the formula (I) which are preferred according to the invention are those in which a combination of the meanings listed above as preferred (preferably) is present.

Compounds of the formula (I) which are particularly preferred according to the invention are those in which a combination of the meanings listed above as particularly preferred is present.

Compounds of the formula (I) which are especially preferred according to the invention are those in which a combination of the meanings listed above are especially preferred if present.

In the definitions of radicals listed above and below, hydrocarbon radicals, such as alkyl or alkenyl—including in combination with heteroatoms, such as alkoxy or alkylthio—are, where possible, in each case straight-chain or branched.

In addition to the Preparation Examples, the following compounds of the formula (IC) may be mentioned specifically:

TABLE A (IC)

| $R^1$ | $R^2$ | $R^3$ | Y | X |
|---|---|---|---|---|
| $C_2H_5$ | Cl | H | $CH_2$ | 4-$NO_2$ |
| $C_2H_5$ | Cl | H | $CH_2$ | 4-$OCF_3$ |

TABLE A-continued (IC)

| R¹ | R² | R³ | Y | X |
|---|---|---|---|---|
| $C_2H_5$ | Cl | H | $CH_2$ | 4-$CF_3$ |
| $C_2H_5$ | Cl | H | $CH_2$ | 4-$SCF_3$ |
| $C_2H_5$ | Cl | H | $CH_2$ | 4-$SCH_3$ |
| $C_2H_5$ | Cl | H | $CH_2$ | 4-$SO_2CH_3$ |
| $C_2H_5$ | Cl | H | $CH_2$ | 4-$SO_2CF_3$ |
| $C_2H_5$ | Cl | H | $CH_2$ | 4-$CO_2CH_3$ |
| $C_2H_5$ | Cl | H | $CHCH_3$ | 4-CN |
| $C_2H_5$ | Cl | H | $CHCH_3$ | 4-$NO_2$ |
| $C_2H_5$ | Cl | H | $CHCH_3$ | 4-Cl |
| $C_2H_5$ | Cl | H | $CHCH_3$ | 4-$OCF_3$ |
| $C_2H_5$ | Cl | H | $CHCH_3$ | 4-$CF_3$ |
| $C_2H_5$ | Cl | H | $CHCH_3$ | 4-$SCF_3$ |
| $C_2H_5$ | Cl | H | $CHCH_3$ | 4-$SCH_3$ |
| $C_2H_5$ | Cl | H | $CHCH_3$ | 4-$SO_2CH_3$ |
| $C_2H_5$ | Cl | H | $CHCH_3$ | 4-$SO_2CF_3$ |
| $C_2H_5$ | Cl | H | $CHCH_3$ | 4-$CO_2CH_3$ |
| $C_2H_5$ | Cl | H | $CH_2CH_2$ | 4-CN |
| $C_2H_5$ | Cl | H | CHCH | 4-CN |
| $C_2H_5$ | Cl | H | $CH_2O$ | 4-CN |
| $C_2H_5$ | Cl | $CH_3$ | $CH_2$ | 4-$NO_2$ |
| $C_2H_5$ | Cl | $CH_3$ | $CH_2$ | 4-$OCF_3$ |
| $C_2H_5$ | Cl | $CH_3$ | $CH_2$ | 4-Cl |
| $C_2H_5$ | Cl | $CH_3$ | $CH_2$ | 4-CN |
| $C_2H_5$ | Cl | $COCH_3$ | $CH_2$ | 4-CN |
| $C_2H_5$ | Br | H | $CH_2$ | 4-CN |
| $C_2H_5$ | Br | H | $CH_2$ | 4-$OCF_3$ |
| $C_2H_5$ | Br | H | $CH_2$ | 4-$SCF_3$ |
| $C_2H_5$ | Br | H | $CH_2$ | 4-$SCH_3$ |
| $C_2H_5$ | Br | H | $CH_2$ | 4-$SO_2CH_3$ |
| $C_2H_5$ | Cl | H | $CH_2$ | 4-$NO_2$ |
| $C_2H_5$ | Br | H | $CH_2$ | 4-$SO_2CF_3$ |
| $C_2H_5$ | Br | H | $CH_2$ | 4-$CO_2CH_3$ |
| $C_2H_5$ | Br | H | $CHCH_3$ | 4-CN |
| $C_2H_5$ | Br | H | $CH_2CH_2$ | 4-CN |
| $C_2H_5$ | Br | H | CHCH | 4-CN |
| $C_2H_5$ | Br | H | $CH_2O$ | 4-CN |
| $C_2H_5$ | Br | $CH_3$ | $CH_2$ | 4-CN |
| $C_2H_5$ | Br | $CH_3$ | $CH_2$ | 4-$NO_2$ |
| $C_2H_5$ | Br | $CH_3$ | $CH_2$ | 4-$OCF_3$ |
| $C_2H_5$ | Br | $CH_3$ | $CH_2$ | 4-Cl |
| $C_2H_5$ | Br | $COCH_3$ | $CH_2$ | 4-CN |
| $C_2H_5$ | $NO_2$ | H | $CH_2$ | 4-CN |
| $C_2H_5$ | $NO_2$ | H | $CH_2$ | 4-$NO_2$ |
| $C_2H_5$ | $NO_2$ | H | $CH_2$ | 4-Cl |
| $C_2H_5$ | $NO_2$ | H | $CH_2$ | 4-$OCF_3$ |
| $C_2H_5$ | $NO_2$ | H | $CH_2$ | 4-$SCF_3$ |
| $C_2H_5$ | $NO_2$ | H | $CH_2$ | 4-$SCH_3$ |
| $C_2H_5$ | $NO_2$ | H | $CH_2$ | 4-$SO_2CH_3$ |
| $C_2H_5$ | $NO_2$ | H | $CH_2$ | 4-$SO_2CF_3$ |
| $CH_3$ | $CO_2Et$ | H | $CH_2$ | 4-CN |
| $CH_3$ | $CO_2Et$ | H | $CH_2$ | 4-$NO_2$ |
| $CH_3$ | $CO_2Et$ | H | $CH_2$ | 4-Cl |
| $CH_3$ | $CO_2Et$ | H | $CH_2$ | 4-$OCF_3$ |
| $CH_3$ | $CO_2Et$ | H | $CH_2$ | 4-$CF_3$ |
| $CH_3$ | $CO_2Et$ | H | $CH_2$ | 4-$SCF_3$ |
| $CH_3$ | $CO_2Et$ | H | $CH_2$ | 4-$SCH_3$ |
| $CH_3$ | $CO_2Et$ | H | $CH_2$ | 4-$SO_2CH_3$ |
| $CH_3$ | $CO_2Et$ | H | $CH_2$ | 4-$SO_2CF_3$ |
| $CH_3$ | $CO_2Et$ | H | $CH_2$ | 4-$CO_2CH_3$ |
| $CH_3$ | $CO_2Et$ | H | $CH_2CH_2$ | 4-CN |
| $C_2H_5$ | Cl | H | $CH_2$ | 4-$NO_2$ |
| $CH_3$ | $CO_2Et$ | H | CHCH | 4-CN |
| $CH_3$ | $CO_2Et$ | H | $CH_2O$ | 4-CN |
| $CH_3$ | $CO_2Me$ | H | $CH_2$ | 4-CN |
| $CH_3$ | $CO_2Me$ | H | $CH_2$ | 4-$NO_2$ |
| $CH_3$ | $CO_2Me$ | H | $CH_2$ | 4-Cl |
| $CH_3$ | $CO_2Me$ | H | $CH_2$ | 4-$OCF_3$ |
| $CH_3$ | $CO_2Me$ | H | $CH_2$ | 4-$CF_3$ |
| $C_2H_5$ | $CO_2Me$ | H | $CH_2$ | 4-CN |
| $C_2H_5$ | $CO_2Me$ | H | $CH_2$ | 4-$NO_2$ |
| $C_2H_5$ | $CO_2Me$ | H | $CH_2$ | 4-Cl |
| $C_2H_5$ | $CO_2Me$ | H | $CH_2$ | 4-$OCF_3$ |
| $C_2H_5$ | $CO_2Me$ | H | $CH_2$ | 4-$CF_3$ |
| $C_2H_5$ | CN | H | $CH_2$ | 4-$NO_2$ |
| $C_2H_5$ | CN | H | $CH_2$ | 4-Cl |
| $C_2H_5$ | CN | H | $CH_2$ | 4-$CF_3$ |
| $C_2H_5$ | CN | H | $CH_2$ | 4-$SCF_3$ |
| $C_2H_5$ | CN | H | $CH_2$ | 4-$SO_2CH_3$ |
| $C_2H_5$ | CN | H | $CH_2$ | 4-$SO_2CF_3$ |
| $C_2H_5$ | CN | H | $CH_2$ | 4-$CO_2CH_3$ |
| $C_2H_5$ | CN | H | $CH_2CH_2$ | 4-CN |
| $C_2H_5$ | CN | H | CHCH | 4-CN |
| $C_2H_5$ | CN | H | $CH_2O$ | 4-CN |
| $C_2H_5$ | $CSNH_2$ | H | $CH_2$ | 4-CN |
| $C_2H_5$ | $CSNH_2$ | H | $CH_2$ | 4-$NO_2$ |
| $C_2H_5$ | $CSNH_2$ | H | $CH_2$ | 4-Cl |
| $C_2H_5$ | $CSNH_2$ | H | $CH_2$ | 4-$OCF_3$ |
| $C_2H_5$ | $CSNH_2$ | H | $CH_2$ | 4-$CF_3$ |
| $C_2H_5$ | $CSNH_2$ | H | $CH_2$ | 4-$SCF_3$ |
| $C_2H_5$ | $CSNH_2$ | H | $CH_2$ | 4-$SCH_3$ |
| $C_2H_5$ | $CSNH_2$ | H | $CH_2$ | 4-$SO_2CH_3$ |
| $C_2H_5$ | Cl | H | $CH_2$ | 4-$NO_2$ |
| $C_2H_5$ | $CSNH_2$ | H | $CH_2$ | 4-$SO_2CF_3$ |
| $CH_3$ | SCN | H | $CH_2$ | 4-CN |
| $CH_3$ | SCN | H | $CH_2$ | 4-$NO_2$ |
| $CH_3$ | SCN | H | $CH_2$ | 4-Cl |
| $CH_3$ | SCN | H | $CH_2$ | 4-$OCF_3$ |
| $CH_3$ | SCN | H | $CH_2$ | 4-$CF_3$ |
| $CH_3$ | SCN | H | $CH_2$ | 4-$SCF_3$ |
| $CH_3$ | SCN | H | $CH_2$ | 4-$SCH_3$ |
| $CH_3$ | SCN | H | $CH_2$ | 4-$SO_2CH_3$ |
| $CH_3$ | SCN | H | $CH_2$ | 4-$SO_2CF_3$ |
| $OC_2H_5$ | $CO_2Et$ | H | $CH_2$ | 4-CN |
| $OC_2H_5$ | $CO_2Et$ | H | $CH_2$ | 4-$NO_2$ |
| $OC_2H_5$ | $CO_2Et$ | H | $CH_2$ | 4-Cl |
| $OC_2H_5$ | $CO_2Et$ | H | $CH_2$ | 4-$OCF_3$ |

If, for example, 5-amino-3-methyl-isothiazole and [4-(4-cyano)phenoxy]phenylacetyl chloride are used as starting substances in the preparation of compounds of the formula (I) according to process (a), the course of the reaction can be represented by the following equation:

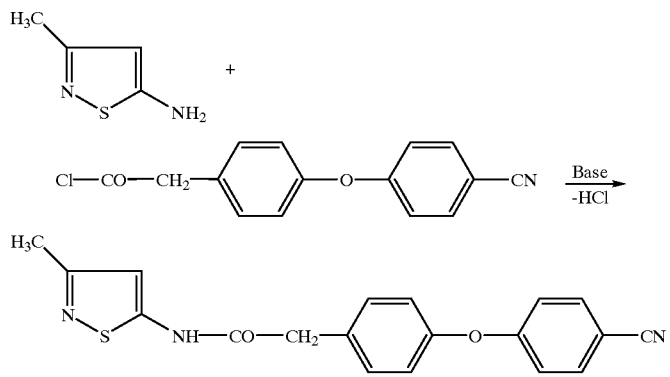

If, for example, 5-[4-(4-cyano)phenoxy]-phenylacetylamino-3-methyl-isothiazole and bromine are used as starting substances in the preparation of compounds of the formula (I) according to process (b/α), the course of the reaction can be represented by the following equation:

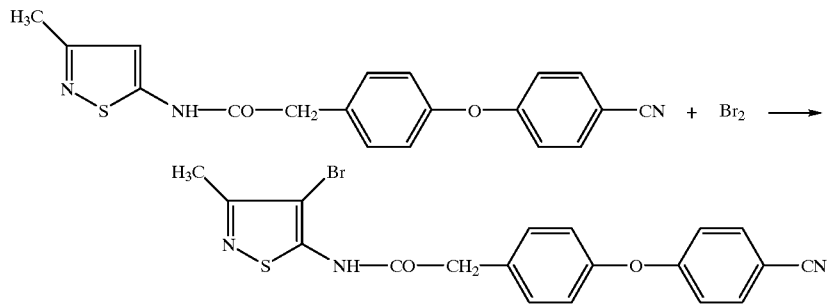

If, for example, 5-[4-(4-cyano)phenoxy]-phenylacetylamino-3-methyl-isothiazole and nitric acid, if appropriate in the presence of acetic acid, are used as the starting substances in the preparation of compounds of the formula (I) according to process (b/β), the course of the reaction can be represented by the following equation:

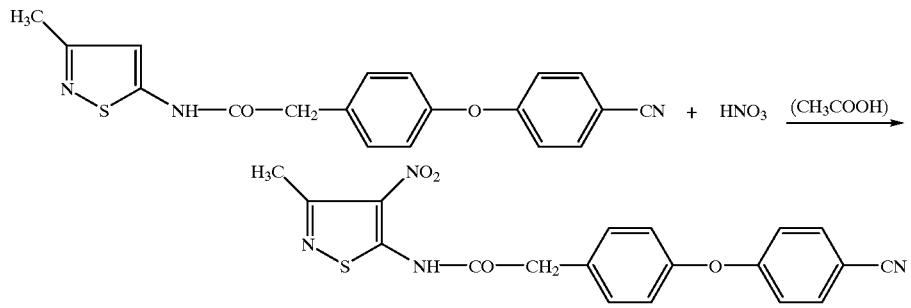

If, for example, β-amino-α-ethoxy-carbonyl-thiocrotonic acid [4-(4-cyano)phenoxy-phenylacetyl]amide is used as the starting substance and H₂O₂ is used as the oxidizing agent in the preparation of compounds of the formula (I) according to process (c), the course of the reaction can be represented by the following equation:

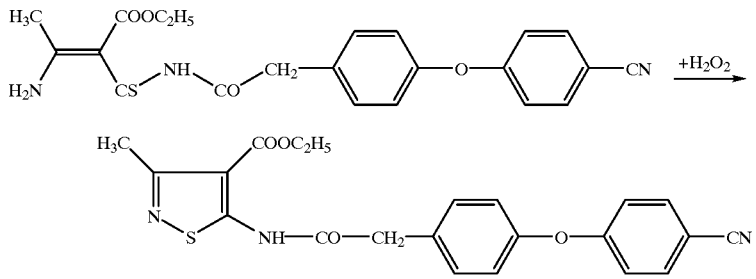

The 5-aminoisothiazoles of the formula (II) to be used as starting substances in process (a) according to the invention are known (cf., for example, DE-A 4 328 425, DE-A 2 249 162, WO-A 93/19 054, WO-A 94/21 617 or J. Het. Chem. 1989, 26, 1575) and/or can be prepared by known methods (cf., for example, the above-mentioned literature references).

The acid halides of the formula (III) furthermore to be used as starting substances in process (a) according to the invention are generally known compounds of organic chemistry. In the formula (III), Hal preferably represents chlorine or bromine.

Formula (IV) provides a general definition of the β-amino-thiocrotonamides to be used as starting substances in process (c) according to the invention. In this formula, $R^1$, $R^4$ and Y preferably, particularly preferably and especially preferably represent those meanings which have already been mentioned above as preferred, particularly preferred and especially preferred for $R^1$, $R^4$ and Y in connection with the description of the compounds of the formula (I) according to the invention. $R^{2-1}$ preferably represents cyano or $C_1$-$C_4$-alkoxycarbonyl, particularly preferably cyano, methoxycarbonyl, ethoxycarbonyl, i-propoxycarbonyl or n-propoxycarbonyl, and especially preferably cyano, methoxycarbonyl or ethoxycarbonyl.

The β-amino-thiocrotonamnides of the formula (IV) are novel. However, they can be obtained in a generally known manner, by a process in which acid halides of the formula (III) are reacted with thiocyanates of the formula (V)

in which

M represents an alkali metal, preferably potassium or sodium, if appropriate in the presence of a diluent, for example a halogenated aliphatic or aromatic hydrocarbon or an ether, nitrile or amide, at temperatures between −40° C. and +120° C., preferably between 0° C. and 80° C., and the compounds formed in this reaction, of the formula (VI)

in which $R^4$ and Y have the above-mentioned meaning, are reacted, preferably directly without isolation, with compounds of the formula (VII)

in which $R^1$ and $R^{2-1}$ have the above-mentioned meaning, if appropriate in the presence of a diluent, for example a halogenated aliphatic or aromatic hydrocarbon or an ether, nitrile or amide, at temperatures between −40° C. and 120° C., preferably between 0° C. and 80° C. (cf. also the general process instructions in J. Org. Chem. 1977, 20, 3230 and Chem. Ber. 1961 94, 2950).

The thiocyanates of the formula (V) and the compounds of the formula (VII) are generally known compounds of organic chemistry.

The process (a) described above for preparation of the compounds of the formula (I) is carried out in the presence of a diluent. All the customary solvents can be employed as diluents.

Diluents which can preferably be used are optionally halogenated aliphatic or aromatic hydrocarbons, ethers or nitrites, such as, for example, cyclohexane, toluene, chlorobenzene, chloroform, methylene chloride, dichloroethane, dioxane, tetrahydrofuran, diethyl ether or acetonitrile.

The process (a) described above for preparation of the compounds of the formula (I) is carried out in the presence of a base.

Bases which can be employed in process (a) are all the customary proton acceptors. Bases which can preferably be used are alkali metal or alkaline earth metal hydroxides, alkali metal or alkaline earth metal carbonates or bicarbonates or nitrogen bases. Examples which may be mentioned are sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction temperatures can be varied within a substantial range in the process (a) described. The reaction is in general carried out at temperatures between −40° C. and +200° C., preferably between 0° C. and 100° C.

In carrying out the process (a) described above for preparation of the compounds of the formula (I), in general 1 to 2 mol, preferably 1 to 1.5 mol, of acid halide of the formula (III) are employed per mole of 5-aminoisothiazole of the formula (II).

In some cases, it has proved advantageous here to employ the 5-aminoisothiazoles of the formula (II) in the form of their hydrohalides, such as, in particular, as hydrochlorides.

Working up and isolation of the end products are carried out in the generally known manner.

The process (b/α) described above for preparation of the compounds of the formula (I) is carried out by means of a halogenating agent.

All the customary halogenating agents can be employed for this process. Halogenating agents which can preferably be used are $Cl_2$, $Br_2$, hydrogen halide acids or salts thereof, such as, for example, sodium hypochlorite and -bromite or potassium hypochlorite and -bromite, $SO_2Cl_2$, $S_2Cl_2$, $PCl_5$ or N-bromosuccinimide.

If appropriate, the process (b/α) described above for preparation of the compounds of the formula (I) is carried out in the presence of a diluent. Diluents which can preferably be used are optionally halogenated aliphatic or aromatic hydrocarbons, ethers, nitriles or amides, such as, for example, cyclohexane, toluene, chlorobenzene, chloroform, methylene chloride, dichloroethane, dioxane, tetrahydrofuran, diethyl ether, acetonitrile or dimethylformamide.

If appropriate, the process (b/α) described above for preparation of the compounds of the formula (I) is carried out in the presence of a catalyst. Catalysts which can be employed are all the acid or basic catalysts customary for a halogenation, such as, for example, hydrogen halides or sodium acetate, and furthermore free radical initiators, such as azoisobutyronitrile or dibenzoyl peroxide.

The reaction temperatures can be varied within a substantial range in the process (b/α) described above. The reaction is in general carried out at temperatures between −40° C. and 120° C., preferably between 0° C. and 80° C.

In carrying out the process (b/α) described above for preparation of the compounds of the formula (I), in general 1 to 2 mol, preferably 1 to 1.5 mol, of halogenating agent are employed per mole of acylated 5-aminoisothiazole of the formula (Ia).

Working up and isolation of the end products are carried out in the generally known manner.

The process (b/β) described above for preparation of the compounds of the formula (I) is carried out by means of a nitrating reagent. All the customary nitrating reagents can be employed for this process. Nitrating reagents which can preferably be used are nitric acid, if appropriate in sulfuric acid, water, acetic acid or acetic anhydride, $N_2O_5$ in carbon tetrachloride, methyl nitrate with $BF_3$, sodium nitrite in trifluoroacetic acid or $N_2O_4$.

If appropriate, the process (b/β) described above for preparation of the compounds of the formula (I) is carried out in the presence of a diluent. Diluents which can preferably be used are optionally halogenated hydrocarbons, such as methylene chloride, chloroform, carbon tetrachloride or chlorobenzene, or nitrobenzene.

The reaction temperatures can be varied within a substantial range in the process (b/β) described above. The reaction is in general carried out at temperatures between 0° C. and 100° C., preferably between 0° C. and 40° C.

In carrying out the process (b/β) described above for preparation of the compounds of the formula (I), in general 1 to 5 mol, preferably 1 to 2 mol, of nitrating reagent are employed per mole of acylated 5-aminoisothiazole of the formula (Ia).

Working up and isolation of the end products are carried out in the generally known manner.

The process (c) described above for preparation of certain compounds of the formula (I) is carried out by means of an oxidizing agent.

Customary oxidizing agents can be employed for this process. Oxidizing agents which can preferably be used are iodine, bromine, chlorine or hydrogen peroxide (in this context, cf. also J. Org. Chem. 1977 20, 3230 and Chem. Ber. 1961, 94, 2950).

If appropriate, the process (c) described above for preparation of certain compounds of the formula (I) is carried out in the presence of a diluent. Diluents which can preferably be used are optionally halogenated aliphatic or aromatic hydrocarbons, ethers, nitriles or amides, such as, for example, cyclohexane, toluene, chlorobenzene, chloroform, methylene chloride, dichloroethane, dioxane, tetrahydrofuran, diethyl ether, acetonitrile or dimethylformamide.

The reaction temperatures can be varied within a substantial range in the process (c) described above. The reaction is in general carried out at temperatures between −40° C. and 120° C., preferably between 0° C. and 80° C.

Working up and isolation of the end products are carried out in the generally known manner.

The active compounds are suitable for controlling animal pests, in particular insects, arachnids and nematodes, which are encountered in agriculture, in forestry, in the protection of stored products and of materials, and in the hygiene field, and have good plant tolerance and favorable toxicity to warm-blooded animals. They may be preferably employed as plant protection agents. They are active against normally sensitive and resistant species and against all or some stages of development. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus Spp., *Macrosiphum avenae,* Myzus spp., *Phorodon humuli, Rhopalosiphum padi,* Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Gelastica alni, Leptinotarsa decemlineata, Phaedon cochleariae*, Diabrotica spp., *Psylliodes chrysocephala, Epilachna varivestis*, Atomaria spp., *Oryzaephilus surinarnensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Omithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp. and Trichodorus spp.

The compounds of the formula (I) according to the invention are distinguished in particular by a high insecticidal and acaricidal activity.

They can be employed particularly successfully for controlling phytopathogenic insects, such as, for example, against the larvae of the mustard beetle (*Phaedon cochlaeriare*), caterpillars of the cabbage moth (*Plutella maculipennis*), the green rice cicada (*Nephotettix cincticeps*) and caterpillars of the owlet moth (*Spodoptera frugiperda*), or for controlling phytopathogenic mites, such as, for example, against the common spider mite (*Tetranychus urticae*).

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and very fine capsules in polymeric substances.

These formulations are produced in a known manner, for example by mixing the active compounds with extenders, that is, liquid solvents, and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example allkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Particularly favorable mixing partners are, for example, the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazol-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinolin sulfate, methyl (E)-2-{2-[6-(2-cyano-phenoxy)-pyrimidine-4-yloxy]-phenyl}-3-methoxyacrylate; methyl (E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, chinomethionate (quinomethionate), chloroneb, chloropicrin, chlorothalonil, chlozolinate, cufraneb, cymoxanil, cyproconazole, cyprofuram, dichlorophen, diclobutrazole, diclofluanid, diclomezin, dichloran, diethofencarb, difenoconazole, dimethirimol, dimethomorph, diniconazole, dinocap, diphenylamine, dipyrithione, ditalimfos, dithianone, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazole, imazalil, imibenconazole, iminoctadin, iprobenfos (IBP), iprodione, isoprothiolan, kasugamycin, copper formulations, such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, penycuron, phosdiphen, phthalide, pimaricin, piperalin, polycarbamate, polyoxin, probenazole, prochloraz, procymidon, propamocarb, propiconazole, propineb, pyrazophos, pyrifenox, pyrimethanil, pyroquilon, quintozene (PCNB), sulfur and sulfur formulations, tebuconazole, tecloftalam, tecnazene, tetraconazole, thiabendazole, thicyofen, thiophanate-methyl, thiram, tolcophos-methyl, tolylfluanide, triadimefon, triadimenol, triazoxide, trichlamide, tricyclazole, tridemorph, triflumizole, triforin, triticonazole, validamycin A, vinclozolin, zineb, ziram.

Bactericides:

bronopol, dichlorophen, nitrapyrin, nickel dimethyldithiocarbamate, kasugamycin, octhilinon, furancarboxylic acid, oxytetracycline, probenazole, streptomycin, tecloftalam, copper sulfate and other copper formulations.

Insecticides/Acaracides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, cloethocarb, clorethoxyfos, chlordenvinphos, chlorfluazuron, chlormephos, chlorpyrifos, chlorpyrifos M, cis-resrnethrin, clocythrin, clofentezin, cyanophos, cycloprothrin, cyflurthrin, cyhalotrin, cyhexatin, cypermethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, ediphenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon, M, oxydeprofos, parathion A, parathion A, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimphos, teflubenzuron, tefluthrin, temephos, terbam, terbufos, tetrachlorovinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides or with fertilizers and growth regulators, is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention act not only against plant, hygiene and stored products pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasite include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderrna spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show an outstanding activity against *Boophilus microplus* and *Lucilia cuprina.*

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10,000-fold dilution, or they can be used as a chemical bath.

It has furthermore been found that the compounds according to the invention also have a potent insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec. *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as

*Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood paneling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water-repellent, if appropriate siccative and UV stabilizers and if appropriate dyestuffs and pigments, as well as other processing auxiliaries.

The insecticidal compositions or concentrates used for preservation of wood and derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Such water-insoluble, oily and oil-like solvents of low volatility which are used as corresponding mineral oils or aromatic fractions thereof or solvent mixtures containing mineral oils, preferably test benzine, petroleum and/or alkylbenzene.

Mineral oils having a boiling range from 170 to 220° C., test benzine having a boiling range from 170 to 220° C., spindle oil having a boiling range from 250 to 350° C., petroleum and aromatics having a boiling range from 160 to 280° C. terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repellent agents, smell correctants and inhibitors or anticorrosive agents and the like which are known per se can additionally be employed.

It is preferred according to the invention for the composition or concentrate to comprise, as the organic chemical binder, at least one alkyl resin or modified alkyl resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulfonic acid esters.

Fixing agents are based chemically on polyvinyl alkyl ethers, such as, for example, polyvinyl methyl ether, or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present Application.

Especially preferred mixing partners which may be mentioned are insecticides, such as chlorpyriphos, phoxim, silafluofin, alphamethrin, cyfluthrin, cyperrnethrin, deltamethrin, permethrin, imidacloprid, NI-25, flufenoxuron, hexaflumuron and triflumuron, and fungicides, such as epoxyconazole, hexaconazole, azaconazole, propioconazole, tebuconazole, cyproconazole, metconazole, imazalil, dichlorfluanid, tolyfluanid, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the following Examples.

PREPARATION EXAMPLES

Example 1

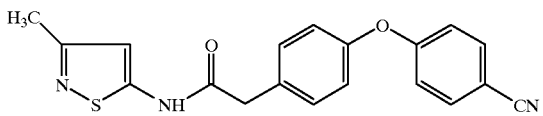

(Process a)

A solution of 5.43 g (0.02 mol) of [4-(4-cyano)phenoxy]-phenylacetyl chloride in 20 ml of acetonitrile is added dropwise to a solution of 3.01 g (0.02 mol) of 5-amino-3-methyl-isothiazole hydrochloride and 3.32 g (0.042 mol) of pyridine in 100 ml of acetonitrile. The mixture is stirred at 25° C. for 18 hours and then concentrated to dryness. The reaction mixture is taken up in water/ethyl acetate and the organic phase is washed several times with 10% strength sodium hydroxide solution. After drying and concentration, a viscous residue is obtained, which is purified by chromatography over silica gel with ethyl acetate as the mobile phase.

2.20 g (31% of theory) of 5-[4-(4-cyano)phenoxy]phenylacetylamino-3-methylisothiazole are obtained.

$^1$H NMR (d$_6$-DMSO): δ=1.18, 2.31, 3.81, 4.04, 6.74, 7.1–7.2, 7.40, 7.82 ppm

Example 2

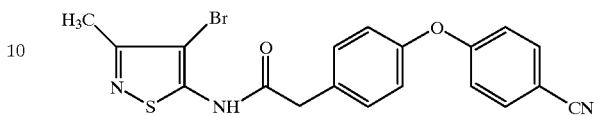

(Process b/α)

0.22 g (0.00134 mol) of bromine in 1 ml of methylene chloride is added dropwise to a solution of 0.40 g (0.00112 mol) of 5-[4-(4-cyano)phenoxy]phenylacetyl-amino-3-methylisothiazole (Example 1) in 10 ml of methylene chloride at 5° C. and the mixture is stirred at 25° C. for 18 hours. After the solvent has been removed in vacuo, 0.50 g (92% of theory) of 4-bromo-5-[4-(cyano)phenoxy]phenylacetamino-3-methylisothiazole of melting point 197–198° C. is obtained.

The following compounds of the formula (I) are obtained analogously or in accordance with the general instructions on the preparation:

TABLE 1

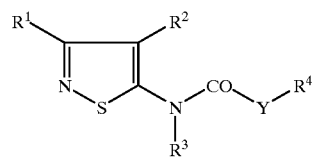

(I)

| Ex. No. | R$^1$ | R$^2$ | R$^3$ | Y | R$^4$ | Physical data ($^1$H NMR; ppm, in d$_6$-DMSO) or melting point (° C.)) |
|---|---|---|---|---|---|---|
| 3 | | | | | | |
| 4 | CH$_3$ | H | H | CH$_2$ | —⟨C$_6$H$_4$⟩—O—⟨C$_6$H$_4$⟩—Cl | 2.31; 3.77; 6.73; 7.00; 7.3–7.5; 12.05 |
| 5 | CH$_3$ | H | H | CH$_2$ | —⟨C$_6$H$_4$⟩—O—⟨C$_6$H$_4$⟩—OCF$_3$ | 2.31; 3.78; 6.73; 7.0–7.1; 7.3–7.4; 12.06 |
| 6 | CH$_3$ | H | H | CH$_2$ | —⟨C$_6$H$_4$⟩—O—⟨C$_6$H$_4$⟩—SCH$_3$ | 137–138 |
| 7 | | | | | | |
| 8 | | | | | | |

TABLE 1-continued
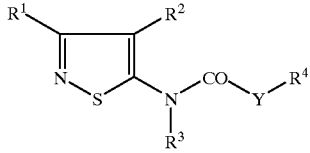
(I)
| Ex. No. | R[1] | R[2] | R[3] | Y | R[4] | Physical data (1H NMR; ppm, in d6-DMSO) or melting point (° C.)) |
|---|---|---|---|---|---|---|
| 9 | CH3 | Br | H | CH2 | 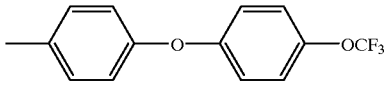 | 189–190 |
| 10 | CH3 | H | H | CH2 | 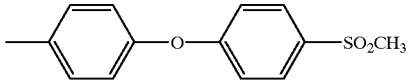 | 2.31; 2.73; 3.80; 6.74; 7.0–7.2; 7.38; 7.70; 12.21 |
| 11 | CH3 | Br | H | CH2 | 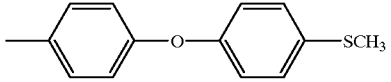 | 2.31; 2.46; 3.75; 7.0–7.1; 7.3–7.4; 7.6–7.7; 12.04 |
| 12 | CH3 | Br | H | CH2 | 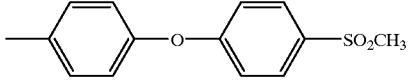 | 2.45; 2.77; 3.94; 7.0–7.1; 7.3–7.4; 7.6–7.7; 8.98*) |
| 13 | CH3 | H | H | CH2 | 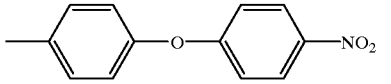 | 2.32; 3.83; 6.74; 7.1–7.2; 7.4–7.5; 8.2–8.3; 12.09 |
| 14 | CH3 | Br | H | CH2 | 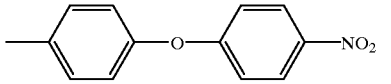 | 2.37; 4.03; 7.0–7.1; 7.4–7.5; 8.2–8.3; 11.59 |
| 15 | | | | | | |
| 16 | C2H5 | CN | H | CH2 | 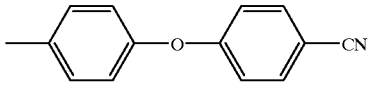 | 1.35; 2.86; 3.94; 6.9–7.5; 9.62*) |
| 17 | C2H5 | CN | H | CH2 | 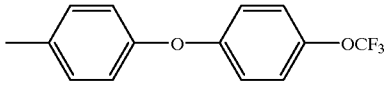 | 1.24; 2.80; 3.97; 4.9–7.4; 12.85 |
| 18 | C2H5 | CN | H | CH2 | 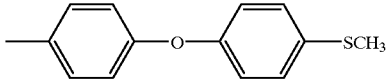 | 1.31; 2.46; 2.84; 3.88; 6.9–7.1; 7.3; 9.21*) |

TABLE 1-continued (I)

$$\text{structure with } R^1, R^2, R^3, R^4, Y \text{ on isothiazole-N-CO-O-Y-R}^4$$

| Ex. No. | $R^1$ | $R^2$ | $R^3$ | Y | $R^4$ | Physical data ($^1$H NMR; ppm, in $d_6$-DMSO) or melting point (°C.)) |
|---|---|---|---|---|---|---|
| 19 | $C_2H_5$ | CN | H | $CH_2$ | –C$_6$H$_4$–O–C$_6$H$_4$–NO$_2$ | 1.24; 2.80; 4.03; 7.0–7.1; 7.20; 8.24; 12.88*) |
| 20 | $CH_3$ | CN | H | $CH_2$ | –C$_6$H$_4$–O–C$_6$H$_4$–CN | 2.53; 3.94; 6.9–7.1; 7.2–7.7*) |
| 21 | $C_4H_9$-t | H | H | $CH_2$ | –C$_6$H$_4$–O–C$_6$H$_4$–CN | 1.30, 3.82; 6.67–7.10; 7.35; 7.60; 8.74 |
| 22 | $C_4H_9$-t | Cl | H | $CH_2$ | –C$_6$H$_4$–O–C$_6$H$_4$–CN | 1.41; 3.90; 6.99; 7.38; 7.61; 8.30*) |
| 23 | $CH_3$ | CN | H | $CH_2$ | –C$_6$H$_4$–O–C$_6$H$_4$–SCF$_3$ | 2.50; 3.99; 6.9–7.1; 7.35; 7.70 |
| 24 | $CH_3$ | CN | H | $CH_2$ | –C$_6$H$_4$–O–C$_6$H$_4$–Cl | 2.50; 3.57; 7.03; 7.3–7.5 |
| 25 | $CH_3$ | CN | H | $CH_2$ | –C$_6$H$_4$–O–C$_6$H$_4$–SCH$_3$ | 2.24; 2.43; 3.96; 6.99; 7.30 |
| 26 | $C_2H_5$ | H | H | $CH_2$ | –C$_6$H$_4$–O–C$_6$H$_4$–CN | 1.26; 2.74; 3.83–5.48; 7.05; 7.27; 7.64*) |
| 27 | $CH_3$ | H | H | $CH_2$ | –C$_6$H$_4$–O–C$_6$H$_4$–SCF$_3$ | 2.50; 3.80; 6.74; 7.09; 7.38; 7.72 |
| 28 | $CH_3$ | H | H | $CH_2O$ | –C$_6$H$_4$–O–C$_6$H$_4$–CN | 175–76 |

TABLE 1-continued
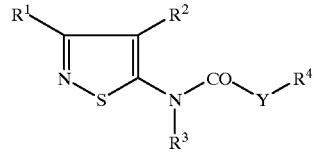
| Ex. No. | R¹ | R² | R³ | Y | R⁴ | Physical data (¹H NMR; ppm, in d₆-DMSO) or melting point (° C.)) |
|---|---|---|---|---|---|---|
| 29 | $CH_3$ | H | H | $CH_2$ | 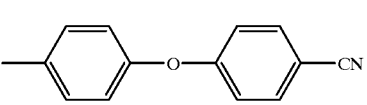 | 198–99 |
| 30 | $CH_3$ | Cl | H | $CH_2O$ | 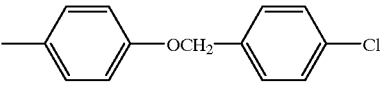 | 175–76 |
| 31 | $CH_3$ | Cl | H | $CH_2$ | 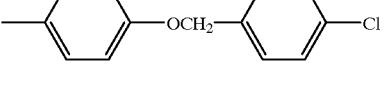 | 2.38; 3.82; 5.07: 6.90, 7.2–7.4*) |
| 32 | $CH_3$ | Br | H | $CH_2$ | 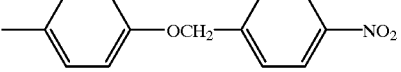 | 2.41; 3.82; 5.07; 7.03; 7.2–7.4*) |
| 33 | $CH_3$ | H | H | $CH_2$ | 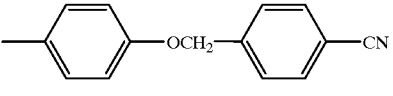 | 154–55 |
| 34 | $CH_3$ | H | H | $CH_2$ | 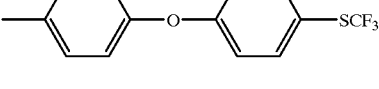 | 184 |
| 35 | $CH_3$ | Cl | H | $CH_2$ | 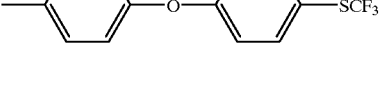 | 59–60 |
| 36 | $CH_3$ | Br | H | $CH_2$ | 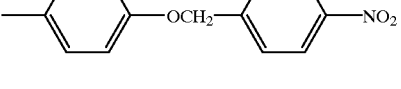 | 60–62 |
| 37 | $CH_3$ | Cl | H | $CH_2$ | 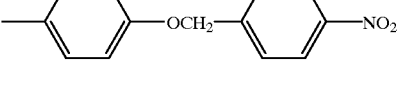 | 178–79 |
| 38 | $CH_3$ | Br | H | $CH_2$ | | 171 |

TABLE 1-continued
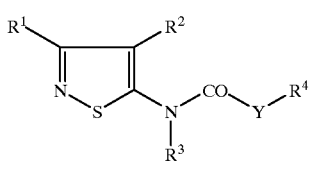
(I)
| Ex. No. | R¹ | R² | R³ | Y | R⁴ | Physical data (¹H NMR; ppm, in d₆-DMSO) or melting point (° C.)) |
|---|---|---|---|---|---|---|
| 39 | CH₃ | Br | H | CH₂ | 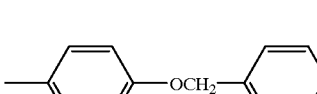 | 168–70 |
| 40 | CH₃ | Cl | H | CH₂ | 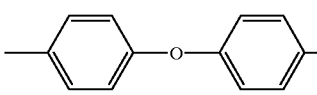 | 211–12 |
| 41 | CH₃ | Br | H | CH₂ | 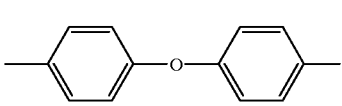 | 2.43; 2.74; 3.89; 7.15; 7.36; 7.65*) |
| 42 | C₂H₅ | Cl | H | CH₂ | 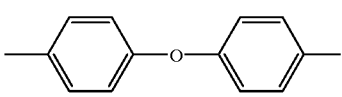 | 185 |
| 43 | C₂H₅ | Br | H | CH₂ | 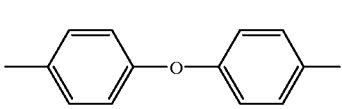 | 196–97 |
| 44 | C₂H₅ | Cl | H | CH₂ | 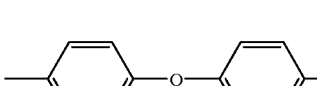 | 1.24; 2.49; 2.73; 3.85; 6.98; 7.28*) |
| 45 | C₂H₅ | Cl | H | CH₂ | 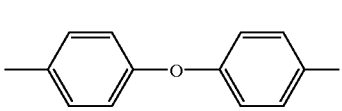 | 90–92 |
| 46 | CH₃ | CN | H | CH₂ | 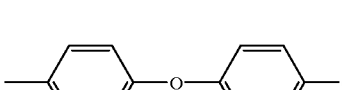 | 198 |
| 47 | C₂H₅ | Br | H | CH₂ |  | 128 |
| 48 | CH₃ | Br | H | CH₂ | | 148–49 |

TABLE 1-continued (I)

Structure: Isothiazole ring with R¹ at 3-position, R² at 4-position, and at 5-position: N(R³)–CO–O–Y–R⁴

| Ex. No. | R¹ | R² | R³ | Y | R⁴ | Physical data (¹H NMR; ppm, in d₆-DMSO) or melting point (° C.) |
|---|---|---|---|---|---|---|
| 49 | $C_2H_5$ | Cl | H | $CH_2$ | –C₆H₄–O–C₆H₄–COCH₃ | 1.28; 2.59; 2.68; 3.89; 7.01; 7.36; 7.94; 8.21*) |
| 50 | $CH_3$ | CN | H | $CH_2$ | –C₆H₄–O–C₆H₄–C(CH₃)=NOCH₃ | 202–03 |
| 51 | $CH_3$ | Br | H | $CH_2$ | –C₆H₄–O–C₆H₄–C(CH₃)=NOCH₃ | 124–25 |
| 52 | $C_2H_5$ | Cl | H | $CH_2$ | –C₆H₄–O–C₆H₄–C(CH₃)=NOCH₃ | 1.28; 2.23; 3.87; 4.00; 6.98; 7.01; 7.32; 7.63; 8.13*) |
| 53 | $C_2H_5$ | Br | H | $CH_2$ | –C₆H₄–O–C₆H₄–C(CH₃)=NOCH₃ | 1.28; 2.22; 3.86; 4.00; 6.99; 7.02; 7.31; 7.62; 8.12*) |
| 54 | $C_2H_5$ | Cl | H | $CH_2$ | –C₆H₄–O–C₆H₄–CS–NH₂ | 1.26; 2.71; 3.89; 6.98; 7.01; 7.35; 7.89*) |
| 55 | $C_2H_5$ | H | H | $CH_2$ | –C₆H₄–O–C₆H₄–(1,2,4-oxadiazol-3-yl) | 160–61 |
| 56 | $C_2H_5$ | Cl | H | $CH_2$ | –C₆H₄–O–C₆H₄–(1,2,4-oxadiazol-3-yl) | 1.29; 2.74; 3.89; 7.12; 7.36; 8.09; 8.12; 8.73*) |

*)in $CDCl_3$

USE EXAMPLES

Example A

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired-concentration.

Cabbage leaves (*Brassica oleracea*) are treated by being dipped into the preparation of the active compound of the desired concentration and are infested with mustard beetle larvae *Phaedon cochleariae*, as long as the leaves are still moist.

After the desired time, the destruction in % is determined. 100% means that all the beetle larvae has been killed; 0% means that none of the beetle larvae has been killed.

In this test, for example, the compounds of Preparation Examples 1, 19, 20, 22, 23, 29, 31, 32, 33, 37, 40, 43, 44, 46, 49, 50, 51, 54 and 55 caused a destruction of 100% after 7 days at an active compound concentration of, for example, 0.1%.

Example B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth *Plutella maculipennis* while the leaves are still moist.

After the desired time, the destruction in % is determined. 100% means that all the caterpillars has been killed; 0% means that none of the caterpillars have been killed.

In this test, for example, the compounds of the Preparation Examples 1 and 19 caused a destruction of 100% after 7 days at an active compound concentration of, for example, 0.1%.

Example C

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth *Spodoptera frugiperda*, as long as the leaves are still moist.

After the desired time, the destruction in % is determined. 100% means that all the caterpillars has been killed; 0% means that none of the caterpillars have been killed.

In this test, for example, the compounds of Preparation Examples 1, 19, 20, 23, 34, 25, 27, 28, 30, 35, 36, 37, 42, 44, 49 and 55 caused a destruction of 100% after 7 days at an active compound concentration of, for example, 0.1%.

Example D

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice cicada *Nephotettix cincticeps*, as long as the seedlings are still moist.

After the desired time, the destruction in % is determined. 100% means that all the cicadas have been killed; 0% means that none of the cicadas has been killed.

In this test, for example, the compounds of Preparation Examples 19, 20, 26, 27, 35, 41, 42, 48 and 51 caused a destruction of 100% after 6 days at an active compound concentration of, for example, 0.1%.

Example E

Tetranychus test (OP-resistant/dipping treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) heavily infested by all development stages of the common spider mite *Tetranychus urticae* are dipped in an active compound preparation of the desired concentration.

After the desired time, the action in % is determined. 100% means that all the spider mites have been killed; 0% means that none of the spider mites has been killed.

In this test, for example, the compound of Preparation Example 1 caused a destruction of 100% after 13 days at an active compound concentration of, for example, 0.01%.

Example F

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested with the peach aphid (*Myzus persicae*) are treated by being dipped into the preparation of the active compound of the desired concentration.

After the desired time, the destruction in % is determined. 100% means that all the aphids have been killed; 0% means that none of the aphids has been killed.

In this test, for example. the compounds according to Preparation Examples 25, 26, 31, 41 and 51 caused a destruction of at least 80% after 6 days at an active compound concentration of, for example, 0.1%.

Example G

Test with *Boophilus microplus* resistant/SP-resistant Parkhurst strain

Test animals: Adult satiated females

Solvent: 35 parts by weight of ethylene glycol monomethyl ether

Emulsifier: 35 parts by weight of nonylphenol polyglycol ether

To produce a suitable formulation, three parts by weight of active compound are mixed with seven parts by weight of the solvent/emulsifier mixture indicated above, and the emulsion concentrate thus obtained is diluted with water to the particular desired concentration.

10 adult *Boophilus microplus* res. are immersed for 1 minute in the active compound preparation to be tested. After transfer to plastic beakers and storage in a controlled-environment chamber, the degree of destruction is determined.

100% here means that all the ticks have been killed; 0% means that none of the ticks has been killed.

In this test, for example, the compounds according to Preparation Examples 1 and 2 cause a degree of destruction of 100% at an active compound concentration of, for example, 20 µg/animal.

Example H

Test with fly larvae/development-inhibiting action

Test animals: All larval stages of *Lucilia cuprina* (OP-resistant) [Pupae and adults (without contact with the active compound)]

Solvent: 35 parts by weight of ethylene glycol monomethyl ether

Emulsifier: 35 parts by weight of nonylphenol polyglycol ether

To produce a suitable formulation, three parts by weight of active compound are mixed with seven parts by weight of the above-mentioned solvent/emulsifier mixture, and the emulsion concentrate thus obtained is diluted with water to the particular desired concentration.

30–50 larvae per concentration are placed on horsemeat (1 cm$^3$) in glass tubes, onto which 500 µl of the dilution to be tested are pipetted. The glass tubes are placed in plastic beakers, the bases of which are covered with marine sand, and kept in a controlled-environment chamber (26° C.±1.5° C., 70% relative humidity±10%). The active compound control is carried out after 24 hours and 48 hours (larvicidal action). After the larvae have migrated (about 72 hours), the glass tubes are removed and perforated plastic lids are placed on the beakers. After 1½ times the development period (hatching of the control flies), the flies which have hatched and the pupae/pupal shells are counted.

Criteria for the action are the onset of death in the treated larvae after 48 hours (larvicidal effect) or the inhibition of hatching of the adult from the pupae or the inhibition of pupation. Criteria for the in vitro action of a substance are the inhibition of flea development or a stop in development before the adult stage. 100% larvicidal action here means that all the larvae have died after 48 hours. 100% development-inhibiting action means that no adult flies have hatched.

In this test, for example, the compounds according to Preparation Examples 1 and 2 had an action of 100% at an active compound concentration of, for example, 1000 ppm.

Example I

Test with cat fleas/development-inhibiting action

Test animals: All stages (eggs, larvae, pupi and adult) of *Ctenocephalides felis*

Solvent: 35 parts by weight of ethylene glycol monomethyl ether

Emulsifier: 35 parts by weight of nonylphenol polyglycol ether

To produce a suitable formulation, three parts by weight of active compound are mixed with 7 parts by weight of the above-mentioned solvent/emulsifier mixture, and the emulsion concentrate thus obtained is diluted with water to the particular desired concentration.

200 µl of this active compound preparation are added to 1.8 g of breeding medium (blood meal medium: 125 parts of marine sand, 20 parts of rat food, 3 parts of blood meal, 2 parts of dried yeast) in disposable tubes of 2.0 cm diameter and the components are mixed homogeneously and dried overnight. A spatula-tip of sieved flea eggs (from artificially infected cats) is then added.

The activity of the active compound preparation is determined every 2 days, up to 1½ times the development time of the control batch, by investigating the batches for development stages of the fleas.

Criteria for the in vitro action of a substance are the inhibition of flea development or a stop in development before the adult stage. 100% here means that no adult fleas developed; 0% means that adult fleas hatched.

In this test, for example, the compound according to Preparation Example 2 had an action of 100% at a concentration of, for example, 100 ppm.

Example K

Test with flies (*Musca domestica*)

Test animals: Adult *Musca domestica*, Reichswald strain (OP-, SP-, carbamate-resistant)

Solvent: 35 parts by weight of ethylene glycol monomethyl ether

Emulsifier: 35 parts by weight of nonylphenol polyglycol ether

To produce a suitable formulation, three parts by weight of active compound are mixed with 7 parts of the above-mentioned solvent/emulsifier mixture, and the emulsion concentrate thus obtained is diluted with water to give the particular desired concentration.

2 ml of this active compound preparation are pipetted onto disks of filter paper (diameter 9.5 cm) in Petri dishes of appropriate size. After the filter disks have dried, 25 test animals are transferred to the Petri dishes and the dishes are covered.

The activity of the active compound preparation is determined after 1, 3, 5 and 24 hours. 100% here means that all the flies have been killed; 0% means that none of the flies has been killed.

In this test, for example, the compound according to Preparation Example 2 had an action of 100% at an active compound concentration of, for example, 1000 ppm.

Example L

Cockroach test

Test animals: *Periplaneta americana*

Solvent: 35 parts by weight of ethylene glycol monomethyl ether

Emulsifier: 35 parts by weight of nonylphenol polyglycol ether

To produce a suitable formulation, three parts by weight of active compounds are mixed with seven parts of the above-mentioned solvent/emulsifier mixture, and the emulsion concentrate thus obtained is diluted with water to the particular desired concentration.

2 ml of this active compound preparation are pipetted onto disks of filter paper (diameter 9.5 cm) in Petri dishes of appropriate size. After the filter disks have dried, 5 test animals *P. americana* are transferred and the dishes are covered.

The activity of the active compound preparation is determined after 3 days. 100% here means that all the cockroaches has been killed; 0% means that none of the cockroaches has been killed.

In this test, for example, the compound according to Preparation Example 2 had an activity of 100% at an active compound concentration of, for example, 1000 ppm.

We claim:

1. Process for the preparation of a compound of the formula (I)

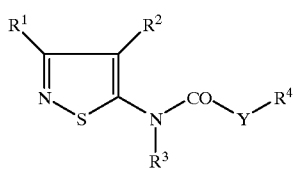 (I)

in which
- $R^1$ represents alkyl, halogenoalkyl, alkoxyalkyl, alkylthioalkyl, alkoxy, alkylthio or optionally substituted cycloalkyl,
- $R^2$ represents halogen or nitro,
- $R^3$ represents hydrogen, alkyl, halogenoalkyl, alkoxyalkyl, alkylcarbonyl, alkylsulfonyl, in each case optionally substituted arylcarbonyl, arylsulfonyl or arylalkyl or optionally substituted cycloalkyl,
- $R^4$ represents optionally substituted aryl, optionally substituted cycloalkyl or optionally substituted cycloalkenyl and Y represents optionally substituted alkylene, alkenylene or alkylenoxy comprising:
reacting a acylated 5-aminoisothiazole of the formula (Ia)

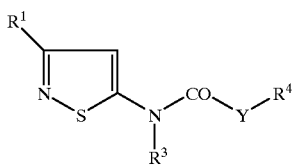 (Ia)

in which
$R^1$, $R^3$, $R^4$ and Y have the abovementioned meaning,
- (α) with a halogenating agent, optionally in the presence of a diluent and optionally in the presence of a catalyst, or
- (β) with a nitrating reagent, optionally in the presence of a diluent.

* * * * *